(12) United States Patent
Kleyman

(10) Patent No.: US 6,579,269 B1
(45) Date of Patent: Jun. 17, 2003

(54) DOSAGE DEVICE

(75) Inventor: Gennady I. Kleyman, 1290 E. 19th St., Suite 3A, Brooklyn, NY (US) 11230

(73) Assignees: Gennady I. Kleyman, Brooklyn, NY (US); GIK Invent & Design, Inc.

( * ) Notice: Subject to any disclaimer, the term of this patent is extended or adjusted under 35 U.S.C. 154(b) by 0 days.

(21) Appl. No.: 09/399,649

(22) Filed: Sep. 21, 1999

(51) Int. Cl.[7] .................................................. A61M 5/00
(52) U.S. Cl. ........................................................ 604/207
(58) Field of Search .............................. 604/181, 187, 604/207, 209, 210, 218, 220, 221, 246, 15, 18, 500

(56) References Cited

U.S. PATENT DOCUMENTS

| | | | |
|---|---|---|---|
| 2,764,981 A | * | 10/1956 | Helmer et al. ............... 604/210 |
| 4,252,159 A | | 2/1981 | Maki |
| 4,357,971 A | | 11/1982 | Friedman |
| 4,466,426 A | * | 8/1984 | Blackman |
| 4,658,993 A | * | 4/1987 | Vlasich ....................... 222/390 |
| 5,127,906 A | * | 7/1992 | Landry, Jr. et al. |
| 5,232,459 A | | 8/1993 | Hjertman |
| 5,279,582 A | * | 1/1994 | Davison et al. ............. 604/198 |
| 5,380,295 A | * | 1/1995 | Vacca ......................... 604/187 |
| 5,385,559 A | | 1/1995 | Mannix |
| 5,741,232 A | | 4/1998 | Reilly et al. |
| 5,795,333 A | | 8/1998 | Reilly et al. |
| 6,168,576 B1 | * | 1/2001 | Reynolds |

* cited by examiner

*Primary Examiner*—Michael Hayes
(74) *Attorney, Agent, or Firm*—Dilworth & Barrese

(57) ABSTRACT

A dosage device includes an outer body and an inner body displaceable relative one another and each formed with formations that engage one another to increase resistance to the displacement and to produce an audible sound corresponding to a predetermined dose of liquid traversing a passage which is formed in the outer body.

5 Claims, 3 Drawing Sheets

DOSAGE DEVICE

FIELD OF THE INVENTION

This invention relates to a dosage device having an audible and tactile mechanism that generates variable sliding resistance that may be accompanied by a sound heard by a person to help him or her in the determination of a desired amount of liquid being passed into and from this device. More particularly, the invention relates to a dosage device provided with a resistance and sound generating mechanism accurately indicating an amount of medicine being passed from the medical container to the interior of the dosage device and dispensed from the syringe during the use thereof.

BACKGROUND OF THE INVENTION

In situations where people have difficulties requiring that they administer certain medicine to themselves there is a persisting problem to accurately transfer the amount of medicine from a container into a syringe and further from the syringe into a body. Such difficulties may include medical problems, such as sight impediments, or body parts not easily accessible or even environmental conditions, for example, darkness. Regardless of these difficulties it is important that the amount of medicine being injected and ejected is accurate.

Another difficulty may arise when a user, typically a construction worker, has to dispense a predetermined amount of medium used for construction purposes in places that are not easily accessible. Similar to difficulties discussed above, the amount of medium to be dispensed has to be accurate.

Attempts have been made in the prior art to overcome these problems and provide some type of structure, which allows a person to accurately transfer the amount of medication to and from a syringe.

The U.S. Pat. No. 4,252,159 to Maki, teaches a dosage device including an elongated slat body on which a syringe is mounted by means of upstanding substantially Y-shaped brackets that are spaced from one another and extending upwardly from a flat exposed surface of the body. An adjustable top member threadedly engages an upstanding internally threaded element provided with externally located lands that, in turn, co-operate with an irregularly shaped knob so as to produce audible signals upon a 360° revolution. The engagement and sound between the above-mentioned elements depends upon a number of factors which may include flexibility of the base or play between the threaded engagement such that the outwardly projected portion of the knob may pass over and in engagement with the lands.

The U.S. Pat. No. 4,466,426 to Blackman, discloses a syringe that has a plunger providing an audible sound upon a plunger being withdrawn from the barrel of a syringe.

The U.S. Pat. No. 4,883,101 to Strong, discloses a device for filling an injection syringe which incorporates a sound indicator provided with mechanical, electrical or an electronic sound device. A spring-loaded ball bearing is biased against a gear wheel and produces a distinctly audible clicking sound when the gear moves a single notch. A user counts the sounds accurately indicating the amount of liquid medicine drawn into the syringe when the attached syringe holder moves.

The U.S. Pat. Nos. 5,741,232 and 5,795,333 to Reilly, disclose a front loading syringe having a movable plunger rotatably on an injector housing. An audible indicating mechanism is activated when the syringe is essentially in the desired mounted position and includes ribs which are function as volumetric gradations.

While the above noted patents are all directed to structures which attempt to overcome problems associated with dispensing proper dosage of medicine, these structure are rather complicated and inconvenient in use. The need therefore arises to have a simple structure of a dosing device that will allow a user to administer medicine in a simple and efficient manner.

SUMMARY OF THE INVENTION

With a device according to the invention one can operate a dosage device, such as a syringe filling assembly, in a conventional manner and still be able to correctly meter dosage amount.

Particularly, the syringe filling assembly in accordance with the invention has a means capable of generating an audible sound as a plunger moves relative to a barrel.

According to one aspect of the invention, the barrel has an inwardly extending formation periodically engaging recesses that are formed in the plunger. The spacing between the recesses is uniform and is dimensioned such that one recess passing by the formation will allow the withdrawal of the plunger to a point at which one volume unit is directed into or out of the dosage device.

In accordance with another aspect of the invention, the barrel is formed with a plurality of formations engageable by an outwardly extending formation that is mounted to the plunger and is shaped to produce an audible sound.

Still another aspect of the present invention is to provide a holder removably mounted on a proximal end of the barrel and having a formation that engages a plurality of the recesses formed on the plunger.

It is therefore an object of the invention to provide a dosage device having a simple structure reliably indicating proper dosage amount.

Still another object of the invention is to provide a dosage device having a structure capable of producing an audible sound corresponding to predetermined dosage amounts entering or leaving the dosage device.

Yet another object of the invention is to provide a dosage device having a barrel with a formation extending toward and periodically engaging a plurality of recesses that are formed on a plunger of the dosage device.

Another object of the invention is to provide a dosage device having a plunger, which is formed with a formation extending toward and periodically engaging a plurality of recesses formed on a barrel of the dosage device.

Yet another object of the present invention is to provide a dosage device having a handle removably mounted to a barrel and formed with a formation that extends toward and periodically engages a plurality of recesses formed on a plunger of the dosage device.

BRIEF DESCRIPTION OF THE DRAWINGS

The above and other objects, features and advantages will become more readily apparent from the following detailed description of a preferred embodiment of the syringe, wherein references being made to the following accompanying drawings.

DETAILED DESCRIPTION OF THE DRAWINGS

Figure 1:
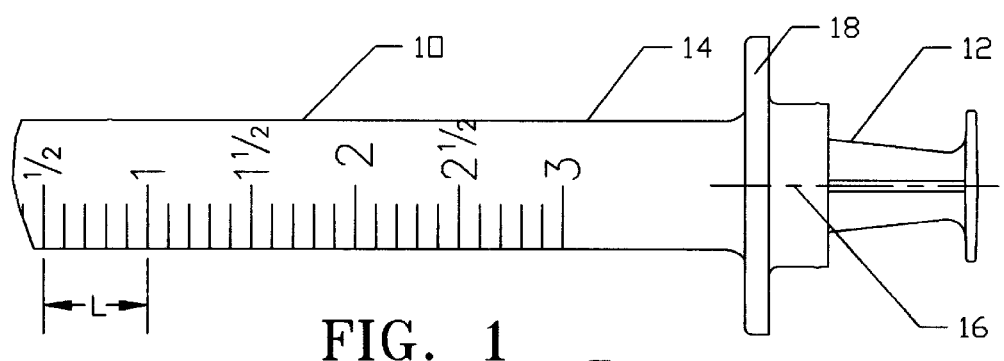
FIG. 1 is an isometric view of a syringe according the invention.

As shown in the accompanying drawings, the present invention is directed to a syringe filling assembly specifically designed to meter out proper doses of liquid medicine and which is generally indicated as 10 in FIG. 1. The assembly includes an elongated barrel 14 extending along a longitudinal axis 16 and receiving a plunger 12, which coaxially slides along the barrel upon applying an external force. A flange 18 provides a support for a user who is able to grasp the flange during filling the barrel as well as during emptying the barrel while administering the medicine. As a standard feature, the barrel 14 has a scale formed on its outer peripheral surface and calibrated in cubic mm so as to enable a user to observe dosage amount of the medicine liquid.

Referring to FIGS. 2–7, the syringe filling assembly is shown according to a few different embodiments having the same concept in common. This concept includes a structure that allows to vary resistance to slidable displacement of the plunger 12 which may be accompanied by an audible sound informing a user who may experience either medical problems or administer a liquid to body parts that are not easily accessible to a user.

Figure 2:
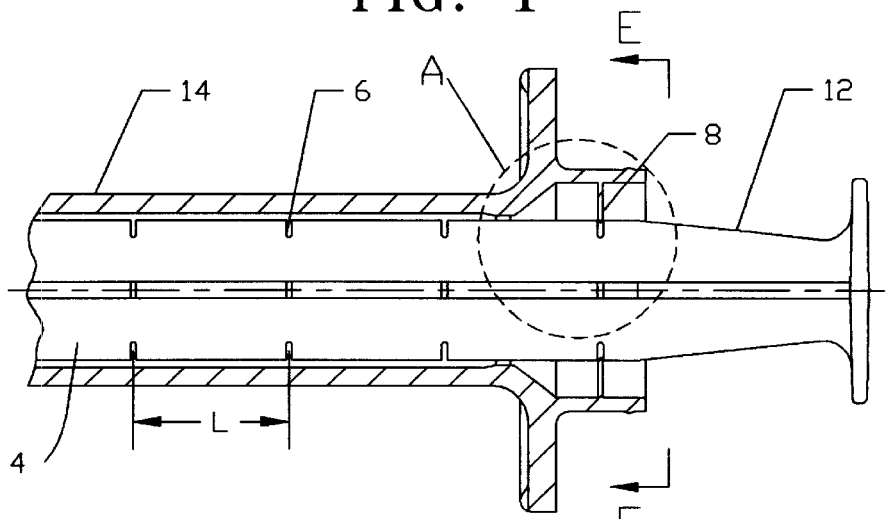
FIG. 2 is a sectional view of the syringe taken along a longitudinal axis and showing a means generating an increased resistance to the sliding displacement of a plunger that is accompanied by an audible sound according to one aspect of the invention.
Figure 3:
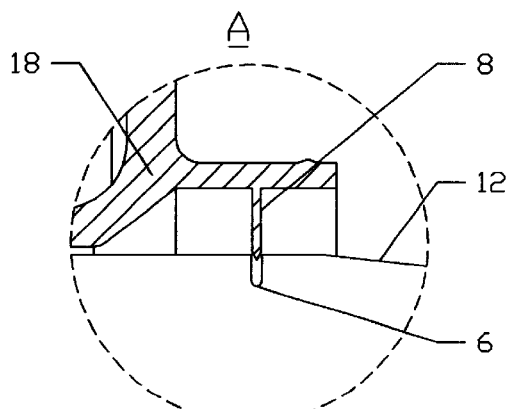
FIG. 3 is an enlarged sectional view of a detail A shown in FIG. 2.
Figure 3A:
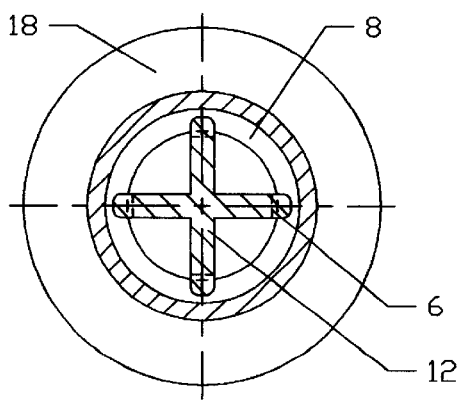

In accordance with one aspect of the invention, the syringe filling assembly shown in FIG. 2 includes the barrel 14 having at least one formation 8 that periodically engages a series of uniformly spaced apart indents 6 recessed in the plunger 12. Adjacent indents 6 are spaced at an interval L corresponding to a predetermined dose of liquid traversing a passage 4 that is formed in the barrel 14.

As the plunger and the barrel are displaced relative to each other, the formation 8 engaging the intent 6 generates a perceptible increase of resistance to displacement that can be easily sensed by a user. This increased resistance is accompanied by an audible sound that in combination with the sensed resistance gives a correct indication of the dosage accumulated in the syringe or evacuated therefrom.

Figure 4:
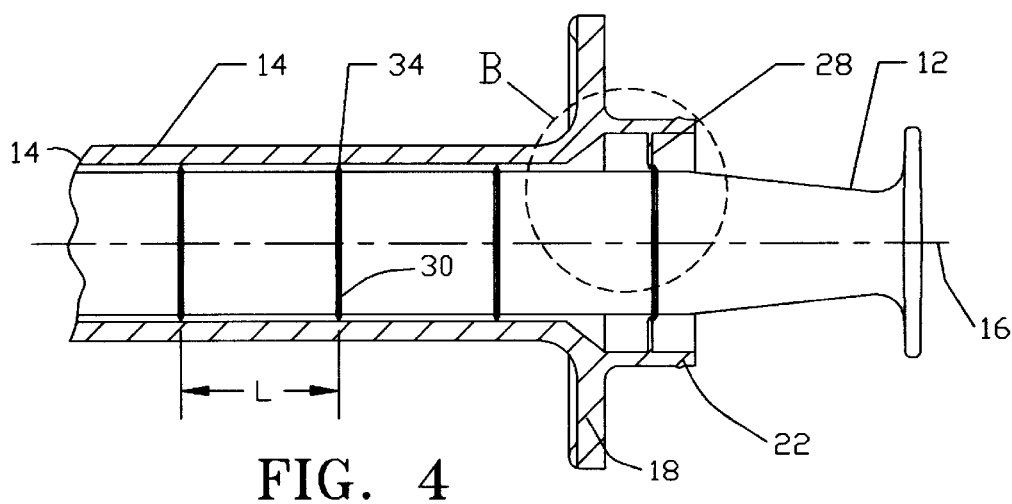
FIG. 4 is a sectional view of the syringe taken along a longitudinal axis and showing a means producing an audible sound according to another aspect of the invention.

Another embodiment of the syringe seen in FIG. 4 includes at least one formation 28 extending from and attached to an axial portion 22 of the flange 18, which has an inner diameter (d) larger than the remaining portion of the barrel 14 (FIGS. 2–7 and 9–10) and extends from a radial finger support 46 towards its outer end.

A user, being sightless or sight impaired, determines the proper distance of displacement of the plunger by counting a number of "clicks" produced by the formations 28 upon encountering protrusions 30 formed on the plunger 12. In this case, gradual withdrawal of the plunger 12 away from the distal end 11 causes a medicine liquid to enter the interior of the barrel at the amount easily identifiable by a number of subsequent clicks that are produced by each protrusion 30 encountering the single formation 28.

Figure 5:
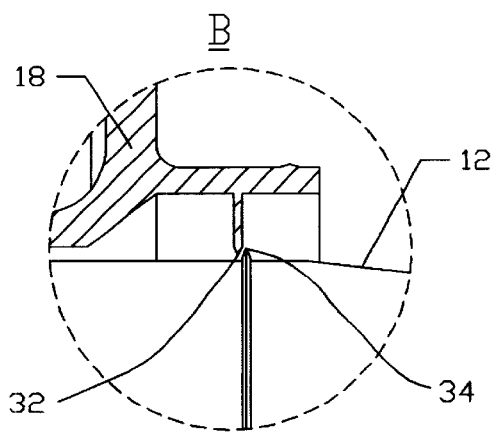
FIG. 5 is an enlarged sectional view of a detail B shown in FIG. 4.

Each of the protrusions 30 as well as formations 28 is made of a flexible material. The distance between neighboring protrusions is equivalent to a distance at which the plunger 12 needs to be displaced so as to allow passage of liquid into or out of the syringe 10 that corresponds to a unit volume such as one cubic centimeter. The tips 32, 34 of the formation 28 and protrusions 30, better seen in FIG. 5, are formed with slanted complementary extending surfaces, so as to provide a sufficient resistance readily sensed by the user's arm upon contact between the formation and protrusion. However, the tips are shaped to allow relatively smooth displacement of the plunger 12 relative to the barrel 14. The tips may overlap each other at a small distance such as 0.05". In examples illustrated in FIGS. 1–10, the tips have conical cross-sections, but any other cross-section meeting the requirements listed above is acceptable.

A number of formations 28 may vary from the single one as discussed above to a plurality of formations equidistantly spaced apart at the same distance as the protrusions 30. Further, as is shown in the drawings, the formations and protrusions extend generally perpendicular to the axis 16. However, it is within the scope of this invention to form these elements so as they angularly extend towards the longitudinal axis 16.

Figure 6:
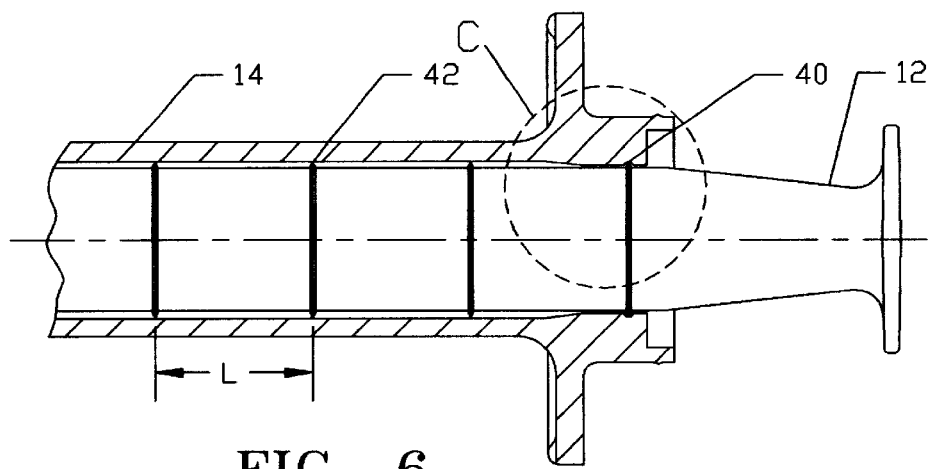
FIG. 6 is a sectional view of the syringe taken along a longitudinal axis and showing a means producing an audible sound according to still another aspect of the invention.
Figure 7:
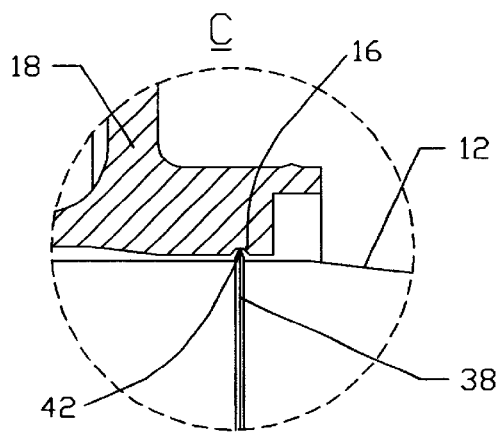
FIG. 7 is an enlarged sectional view of a detail C shown in FIG. 6.

According to another aspect of the invention illustrated in FIGS. 6 and 7, the barrel 14 has an axial proximal end 38 formed with a recess 40 receiving tips 42 of the protrusions 38 that are formed on the plunger 12.

Similarly to the embodiment discussed above, the protrusions 38 are equidistantly spaced apart at a distance corresponding to a predetermined amount of medicine liquid that passes into or from the barrel 14. A decreased resistance to axial displacement of the plunger 12 is easily sensed as the protrusions 38 sequentially engage the recess 40 of the barrel 14. A number and shape of recesses may vary as is explained in reference to FIGS. 2 and 4.

Figure 8:
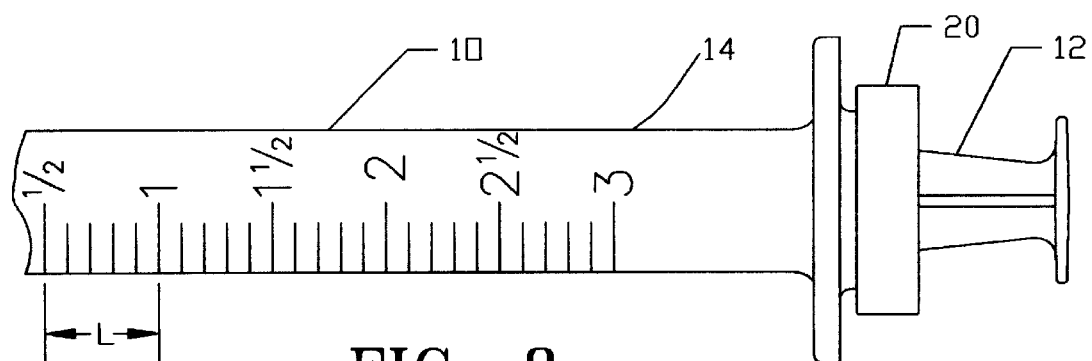
FIG. 8 is an isometric view of a syringe according to another embodiment of the invention.
Figure 9:
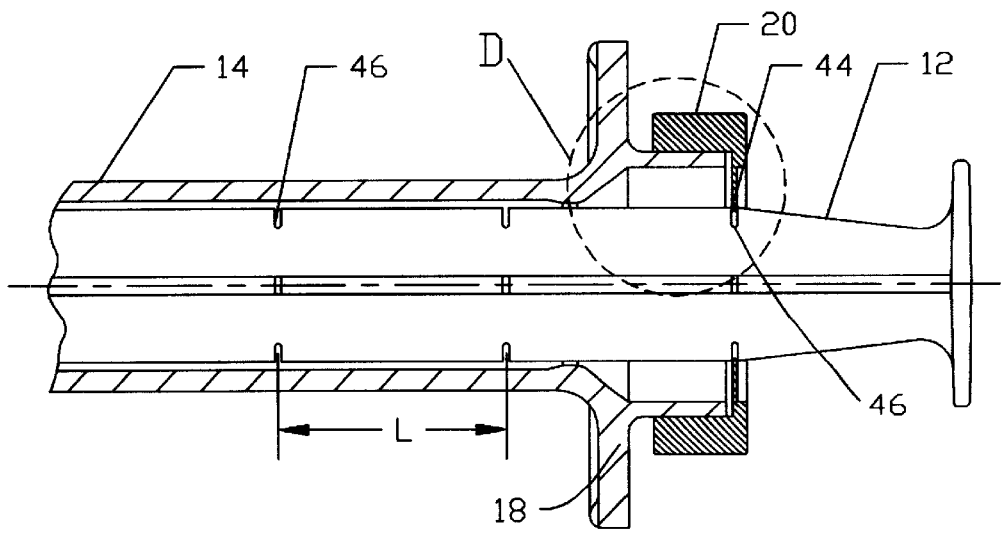
FIG. 9 is a sectional view of the syringe taken along a longitudinal axis of the syringe shown in FIG. 8.
Figure 10:
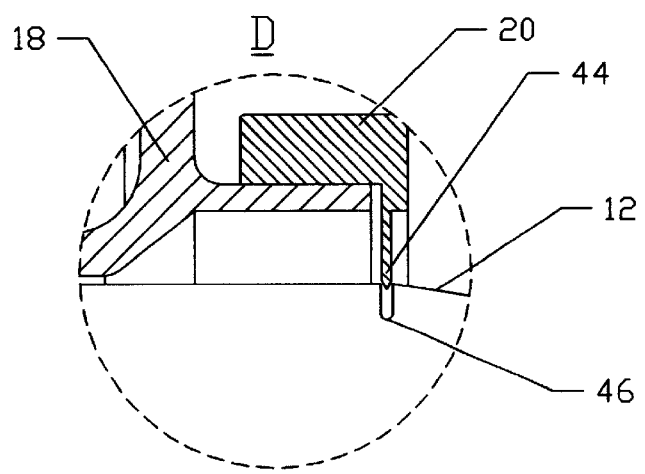
FIG. 10 is an enlarged sectional view of a detail D shown in FIG. 9.

In accordance with still another aspect of the invention, the head 20 as illustrated in FIGS. 8–10, is mounted to a flange 43 of the barrel 12 such that the head is axially fixed with the barrel. The head is preferably annular and has an L shape, wherein a leg 44 extends toward and sequentially engages a plurality of recesses 46 formed in the plunger 12 of the syringe assembly 10. Similarly to the embodiments described above, relative displacement of the assembly's parts in and from a position, wherein the leg 44 is aligned with each of the recesses 46, results in a click.

In operation, the plunger 12 is displaced toward the distal end of the barrel 14 corresponding to an initial position, wherein the formations formed on the plunger and barrel are aligned. Further displacement of the plunger toward a proximal end of the barrel is accompanied by a number of clicks as the formation on the plunger passes the formations formed either on the barrel and/or on the head 20. As described herein above, each sound is indicative of a specified dose of the medical liquid filling the barrel.

Reverse displacement of the plunger towards the distal end of the barrel is also accompanied by a number of clicks informing the user how much liquid has been administered into his or her body.

While the dosage device of the invention has been described to be adapted for injection, it may be applicable to other systems, angiographic and otherwise. It is therefore understood the foregoing description and accompanying drawings set fort the preferred embodiment of the invention. Various modifications, additions and alternative designs will, of course, become apparent in light of the foregoing teaching without departing from the scope of the disclosed invention as recited in the appended claims.

What is claimed is:

1. A dosage device for administering fluid medium, comprising
    a sleeve having an inner surface defining a passage, which is traversed by the fluid medium, the sleeve being provided with:
        a distal, relatively long annular portion,
        a proximal, relatively short annular portion,
        an intermediary annular portion bridging the distal, relatively long and proximal, relatively short annular portions and widening toward the proximal, relatively short annular portion, and
        an annular flange located on the intermediary annular portion and extending radially outwards therefrom;
    a plunger slidably mounted in the sleeve to enable the fluid medium to pass into and from the passage; and
    a protrusion provided on the inner surface of the sleeve in the vicinity of the proximal, relatively short annular portion and extending radially inwardly toward the plunger which has a plurality of spaced formations slidably engaging the protrusion to vary resistance to the displacement of the plunger and to allow a user to determine a desirable dosage of medium egressed from or ingressed in the sleeve in response to an audible sound produced by the protrusion when the spaced formations slip out of engagement with the protrusion.

2. The dosage device according to claim 1, further comprising a plurality of spaced indents formed on an outer surface of the plunge and dimensioned so that during displacement of the plunger, the protrusion sequentially engages the spaced indents to produce an audible sound after the user has applied an increased force sufficient to advance the plunger out of the engagement between the protrusion and a respective one of indents.

3. The dosage device according to claim 2, wherein the protrusion is dimensioned to slightly overlap the indents in a radial direction to produce an audible sound as the plunger continues to move relative to the sleeve in response to an increased external force applied by the user.

4. The dosage device according to claim 2, wherein the protrusion has an inner peripheral surface shaped complementary to an outer end surface of each of the spaced indents to prevent permanent interlocking between the protrusion and the spaced indents during relative displacement of the plunger as the external force is being applied.

5. The dosage device according to claim 1, wherein the plunger and the sleeve are made from elastomeric material.

* * * * *